US010428303B2

(12) United States Patent
Gilbert et al.

(10) Patent No.: US 10,428,303 B2
(45) Date of Patent: Oct. 1, 2019

(54) EMBRYO CULTURE METHODS AND MEDIA

(71) Applicant: FUJIFILM Irvine Scientific, Inc., Santa Ana, CA (US)

(72) Inventors: Rebecca Gilbert, Irvine, CA (US); Hsiao-Tzu Ni, Irvine, CA (US); Suh-Fon Hwan, Shanghai (CN)

(73) Assignee: FUJIFILM Irvine Scientific, Inc., Santa Ana, CA (US)

( * ) Notice: Subject to any disclaimer, the term of this patent is extended or adjusted under 35 U.S.C. 154(b) by 0 days.

(21) Appl. No.: 14/327,503

(22) Filed: Jul. 9, 2014

(65) Prior Publication Data

US 2015/0018605 A1 Jan. 15, 2015

Related U.S. Application Data

(60) Provisional application No. 61/844,345, filed on Jul. 9, 2013.

(51) Int. Cl.
*C12N 5/00* (2006.01)
*C12N 5/02* (2006.01)
*C12N 5/073* (2010.01)
*A61B 17/43* (2006.01)

(52) U.S. Cl.
CPC ............ *C12N 5/0604* (2013.01); *A61B 17/43* (2013.01); *C12N 2500/30* (2013.01)

(58) Field of Classification Search
None
See application file for complete search history.

(56) References Cited

U.S. PATENT DOCUMENTS

| | | | |
|---|---|---|---|
| 6,586,247 B1 | 7/2003 | Kaneko | |
| 2002/0028509 A1 | 3/2002 | Choay et al. | |
| 2003/0091972 A1 | 5/2003 | Gardner et al. | |
| 2004/0082062 A1 | 4/2004 | Robertson et al. | |
| 2005/0019906 A1* | 1/2005 | Cecchi | C12N 5/0604 435/366 |
| 2005/0064589 A1 | 3/2005 | Kaplan | |
| 2011/0250690 A1* | 10/2011 | Craig | A01N 1/02 435/404 |

FOREIGN PATENT DOCUMENTS

| | | |
|---|---|---|
| JP | 2010-525818 | 7/2010 |
| WO | WO 00/32140 | 6/2000 |
| WO | WO-2008/134220 | 11/2008 |
| WO | WO 2013/087755 | 6/2013 |

OTHER PUBLICATIONS

Yeung et al., Improved development of human embryos m vitro by a human oviductal cell co-culture system. Human Reproduction, 7:1144-1149, 1992.*

Ridha-Barzanchi et al., Outcome of Baghdad culture medium and in vitro fertilization of human eggs and embryo transfer outcome. Fac Med Baghdad, 2005; vol. 47,355-359.*

Gardner et al., Mouse embryo cleavage, metabolism and viability: role of medium composition. Human Reproduction 8: pp. 288-295. 1993.*

Feichtinger et al., The Use of Synthetic Culture Medium and Patient Serum for Human in Vitro Fertilization and Embryo Replacement. Journal of in Vitro Fertilization and Embryo Transfer, vol. J, No. 2, 1986. p. 87-92.*

Staessen et al., Controlled comparison of commercial media for human in-vitro fertilization: Menezo B2 medium versus Medi-Cult universal and BMI medium. Human Reproduction vol. 13 No. 9 pp. 2548-2554, 1998.*

Mahadevan et al., Improved Human Zygote Development in a Modified Ham's F10 Medium in Vitro.Journal of Assisted Reproduction and Genetics, vol. 13, No. 9, 1996, pp. 722-725.*

Hoogendijk et al., A study of two sequential culture media impact on embryo quality and pregnancy rates. SAJOG, 2007, 13:52-58.*

Rosenkrans et al., Development of Bovine Embryos In Vitro as Affected by Energy Substrates. Biology of Reproduction 49, 459-462 (1993). (Year: 1993).*

Gardner, et al., "Concentrations of nutrients in mouse oviduct fluid and their effects on embryo development and metabolism in vitron*", J. Reprod. Fert. (1990) 88, 361-368.

PCT/US2014/046051 International Search Report, dated Nov. 14, 2014.

Karja et al., Development to the blastocyst stage, the oxidative state, and the quality of early developmental stage of porcine embryos cultured in alteration of glucose concentrations in vitro under different oxygen tensions, Reproductive Biology and Endocrimology, Biomed Central Litd., GB, vol. 4, No. 1, Nov. 6, 2006, 12 pages.

Origio: Safety Data Sheet Universal IVF Medium, Jun. 12, 2006, http://www.origio.com/document/pm9aw34bo6r-1031-1030-Universal-IVF-Medium-SDS-v-8.pdf [retrieved on Oct. 19, 2016], 2 pages.

Gardner et al., "Enhanced Rates of Cleavage and Development for Sheep Zygotes Cultured to the Blastocyst Stage in Vitro in the Absence of Serum and Somatic Cells: Amino Acids, Vitamins, and Culturing Embryos in Groups Stimulate Development" Biology of Reproduction, 1994, 50(2):390-400.

Leese et al. "Metabolism of the viable mammalian embryo: quietness revisited," Mol. Hum. Reproduction (2008) 14(12): 667-72.

Tervit et al., "Successful Culture in Vitro of Sheep and Cattle Ova", J. Reprod. Fertil., 1972, 30:493-497.

Thompson et al., "Oxygen uptake and carbohydrate metabolism by in vitro derived bovine embryos", Journal of Reproduction and Fertility, 1996, 106:299-306.

Hoogendijk et al., "A study of two sequential culture media-impact on embryo quality and pregnancy rates", South African Journal of Obstetrics and Gynaecology, Apr. 2007, vol. 13, No. 2, 7 pages.

(Continued)

*Primary Examiner* — Christopher M Babic
*Assistant Examiner* — Arthur S Leonard
(74) *Attorney, Agent, or Firm* — Foley & Lardner LLP

(57) ABSTRACT

Improved methods of culturing embryos in media having amounts of lactate that have not previously been recognized as beneficial for embryo development. Also, compositions, devices and kits related to the same.

17 Claims, 2 Drawing Sheets

(56) References Cited

OTHER PUBLICATIONS

Mahadevan et al., "Improved Human Zygote Development in a Modified Ham's F10 Medium in Vitro", Journal of Assisted Reproduction and Genetics, 1996, 13(9), 4 pages.

Matsumoto et al., "Effect of glucose and lactate on development of in vitro produced bovine embryos in a modified synthetic oviduct fluid medium", Journal of Mammalian Ova Research, 1999, vol. 16 (4 pages). (with Abstract).

Meseguer et al., "Embryo incubation and selection in a time-lapse monitoring system improves pregnancy outcome compared with a standard incubator: a retrospective cohort study", Fertility and Sterility, 2012, 98(6):1481-1489.

Gardner, et al., "Concentrations of nutrients in mouse oviduct fluid and their effects on embryo development and metabolism in vitro*", J. Reprod. Fert. (1990) 88, 361-368.

Wales, et al., "The Metabolism of Specifically Labelled Lactate and Pyruvate by Two-Cell Mouse Embryos", J. Reprod. Fert. (1973) 33, 207-222.

* cited by examiner

EMBRYO CULTURE METHODS AND MEDIA

CROSS REFERENCE TO RELATED APPLICATION

This application claims the benefit under 35 U.S.C. § 119(e) of the following provisional application, all of which is incorporated herein by reference in its entirety: U.S. Ser. No. 61/844,345, entitled "Embryo Culture Methods and Media," filed Jul. 9, 2013.

BACKGROUND

Field

The present application generally relates to methods and compositions for embryo culture. In particular, the methods and compositions generally relate to media and methods of using media having amounts of lactate that have not previously been recognized as beneficial for embryo development.

Description of the Related Art

Infertility generally refers to not being able to become pregnant after some period of time, such as one year of unprotected sex. It is estimated that approximately 6% of women in the U.S. experience infertility. In the UK, some reports suggest that about 14% of couples experience fertility challenges. The lack of fertility can be attributable to either gender or both the male and female. Any of a number of factors can contribute to or be the primary cause of the infertility. Such factors include damage to DNA, genetic factors, health or other disease factors in either partner, toxins, immune system challenges, hormonal and other endocrine factors, infections caused by viruses or other microorganisms, and the like.

In vitro fertilization (IVF) is one approach to assisting in achieving a successful pregnancy for a couple that otherwise may be infertile. IVF is a process by which an egg from a mother is fertilized by a sperm outside of the body, or in vitro. Despite being successful in many cases, IVF methods stand to gain from improvements in technology and methodology. Some embodiments described herein relate to improved methods and compositions for embryo culture, which can improve IVF and cell culture methods.

SUMMARY OF THE INVENTION

This invention is predicated on the surprising discovery that culturing embryos in a medium that has a lactate concentration within a range that previously has not been utilized for culturing of human embryos or for IVF protocols can lead to improved embryo development and healthier embryos.

In one embodiment, disclosed herein is a method of culturing a human embryo in vitro, comprising providing a medium comprising a starting lactate concentration of less than 3 mM and culturing a human embryo in said medium. In a preferred embodiment, the lactate concentration is between 0 mM and 3 mM, or any value or subrange there between.

The medium may be any medium suitable for culturing a mammalian embryo. The amount of lactate in some embodiments can be less than the amount present in the reproductive system of the mother of the mammalian embryo. In a preferred embodiment, the medium is a medium suitable for culturing a human embryo. In one embodiment, the medium is a medium suitable for culturing an embryo from an endangered species. In one embodiment, the medium is a medium suitable for culturing an embryo from a domesticated species. In one embodiment, the embryo is from a patient suffering from infertility or undergoing fertility treatment.

In one embodiment, the medium is a complex tissue culture media. In a preferred embodiment, the medium is a simple salt solution with added energy substrate(s). In another preferred embodiment, the medium is a sequential media.

In one embodiment, the medium is a modified version of any of the following: Continuous Single Culture™ media (Irvine Scientific), any Global® media (LifeGlobal), G1 medium (Vitrolife), G2 Medium (Vitrolife), a Human Tubal Fluid (HTF) medium with or without glucose or phosphate, Whitten's Medium, Ham's F-10 Medium, or Sage Media, with or without protein supplementation. In one embodiment, the medium is a novel medium not previously published or commercialized.

In one embodiment, the medium is a sequential media system which requires replacement with different media at different stages during embryo development. In one embodiment, the medium is a single, non-sequential or uninterrupted medium that is replenished at least once during the culturing of the embryo. In one embodiment, the medium is a continuous medium that is not replenished during the culturing of the embryo.

In one embodiment, the embryo is cultured in an incubator. In one embodiment, the incubator comprises an imaging system to capture one or more images of the embryo during culturing. In one embodiment, the one or more images can be captured without moving the embryo.

In one embodiment, the embryo is cultured for about 1 day to about 7 days. In a preferred embodiment, the embryo is cultured for about 3 days to about 6 days. In one embodiment, the embryo is cultured until it reaches an 8-cell stage or a blastocyst stage.

In one embodiment, the embryo is implanted into a female patient. In one embodiment, the embryo is cryopreserved.

This invention further relates to a composition for culturing a human embryo, comprising an embryo culture medium modified to have a lactate concentration of less than about 3 mM.

DETAILED DESCRIPTION OF THE PREFERRED EMBODIMENT

Figure 1:
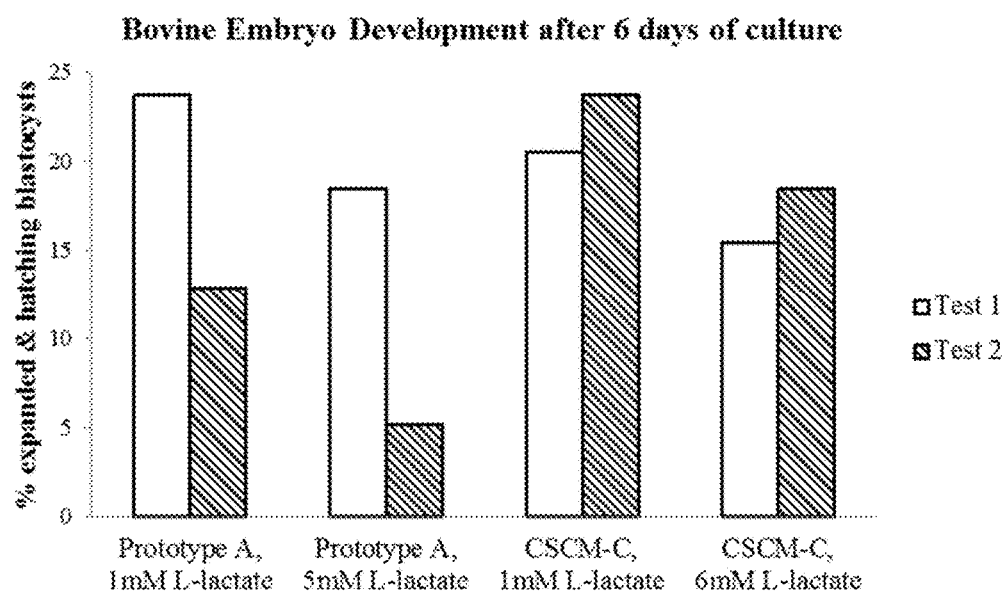
FIG. 1 represents the percentage of bovine embryos in the expanded and hatching blastocyst stages after 6 days of culture in 1 mM or at least 5 mM L-lactate in two different media backbones (Prototype A and Continuous Single Culture Medium-Complete [CSCM-C]).

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

In vitro fertilization (IVF) is the process of fertilization of an egg (oocyte) with sperm outside of the body of the mother in a laboratory dish. The fertilized egg, or embryo, is usually cultured in vitro for some period of time or until a desired developmental milestone is reached. For example, some embryos are cultured until the embryo reaches 6-8 cells, or until reaching the blastocyst stage. Other embryos may be cultured for a period of time such as 5 or 6 days, for example. After the desired culturing has been accomplished, embryo selection and embryo transfer occur by which an embryo is selected and transferred into the uterus of a female patient, and/or in some cases preserved (e.g., cryopreservation) for later implantation.

In some embodiments, the embryo is transferred into a patient suffering from infertility. In some embodiments, the embryo is transferred into a patient undergoing fertility treatments. In some embodiments, the embryo is transferred into a surrogate. That is, the embryo need not be transferred back to the patient who provided the oocyte. In some embodiments, the embryo is cryopreserved. In some embodiments, a cryopreserved embryo is later transferred to a female patient.

Embodiments described herein generally relate to methods of culturing embryos in a medium that has a lactate concentration within range that previously has not been utilized for culturing of human embryos or for IVF protocols. The methods can lead to improved embryo development and healthier embryos.

Most existing media that are used for human embryo culturing have a concentration that approximates the amount found naturally in the reproductive system of the mother in vivo. However, some embodiments described herein are based upon the discovery that culturing an embryo in vitro in a medium having a lactate concentration less than what is found naturally in the mother in vivo can lead to improved embryo development. For example, less than 3 mM lactate concentration can be used for human embryo culture.

Thus, some embodiments herein are generally related to methods of culturing an embryo in vitro in a medium for embryo culture that has a lactate concentration less than the concentration found in vivo in the mother for a given species. For example, the amount can be between 0% and 90% of the concentration generally found in the mother, or any value or subrange there between. Examples of embryos that can be cultured utilizing the methods described herein include any animal cell, but preferably include mammalian embryos. Mammalian embryos that can be used include, without limitation, bovine, equine, porcine, canine, feline, ovine, simian, lupine, murine, leporine, and more preferably include human or *homo sapien* embryos. In one embodiment, the embryo is from an endangered species. In one embodiment, the embryo is from a domesticated species (e.g., cattle, horses, sheep, pigs, dogs, cats, and the like, without limitation). In another embodiment, the embryo is from a non-human primate. It should be understood that one or more of the species listed above can be specifically excluded from one or more of the methods described herein.

For example, in the case of a human embryo, without being limited thereto, the medium can have a lactate concentration that is less than about 3 mM, for example, or any value or subrange there between (e.g., about 0 mM to about 0.4 mM, about 0.5 mM, about 0.6 mM, about 0.7, mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, about 2 mM, about 2.1 mM, about 2.2 mM, about 2.3 mM, about 2.4 mM, about 2.5 mM and so on; or between about 0.5 mM and about 3 mM, about 0.6 mM and about 2.5 mM, etc.). The medium can have such a lactate concentration as its initial concentration without further supplementation for a desired time period of culture, e.g., throughout the culture time period (as discussed below).

The medium can be any suitable medium for embryo culture, including, for example, a sequential medium or a single medium that is replenished at least once during the culture process, or a non-sequential medium or a medium that is not replenished (e.g., uninterrupted or continuous culture) during the culturing of the embryo. Existing media that are known to those of skill in the art or that are commercially available can be modified to have a lactate concentration as described herein (e.g., less than 3 mM for certain non-limiting human embryo culture). Some non-limiting examples of existing media that can be utilized in the methods or that can be modified for use include, without limitation, Continuous Single Culture™ media (Irvine Scientific), any Global® media (LifeGlobal), G1 medium (Vitrolife), G2 medium (Vitrolife), a Human Tubal Fluid (HTF) medium, HTF medium with or without glucose or phosphate, Whitten's Medium, Ham's F-10 Medium, Sage Media, and the like, with or without protein supplementation. In one embodiment, the medium is a novel medium not previously published or commercialized.

Components of published exemplary, non-limiting media that may be modified for use in the present invention are given in Table 1. Components of exemplary, non-limiting media based on currently available Irvine Scientific culture media that may be modified for use in the present invention are given in Tables 2-6.

TABLE 1

Embryo Culture Media

| Component (mM) | HTF | G1 | G2 | P1 | KSOM |
|---|---|---|---|---|---|
| Sodium pyruvate | 0.3 | 0.32 | 0.1 | 0.33 | 0.2 |
| Sodium lactate | 21.4 | 10.5 | 5.87 | 21.4 | 10 |
| Glucose | 2.78 | 0.5 | 3.15 | — | 0.2 |
| Sodium Chloride | 101.6 | 85.16 | 85.16 | 101.6 | 95 |
| Potassium Chloride | 4.69 | 5.5 | 5.5 | 4.69 | 2.5 |
| Magnesium Sulfate | 0.2 | 1.0 | 1.0 | 0.2 | 0.2 |
| Calcium Chloride | 2.04 | 1.8 | 1.8 | 2.04 | 1.71 |
| Potassium Phosphate | 0.37 | — | — | — | 0.35 |
| Sodium Phosphate | — | 0.5 | 0.5 | — | — |
| Sodium Bicarbonate | 25.0 | 25.0 | 25.0 | 25.0 | 25.0 |
| EDTA | — | 0.01 | — | — | 0.01 |
| Alanine | — | 0.1 | 0.1 | — | — |
| Asparagine | — | 0.1 | 0.1 | — | — |
| Aspartate | — | 0.1 | 0.1 | — | — |
| Glutamate | — | 0.1 | 0.1 | — | — |
| Glutamine (or alanyl-glutamine) | — | 1.0 | 1.0 | — | 1.0 |
| Glycine | — | 0.1 | 0.1 | — | — |
| Proline | — | 0.1 | 0.1 | — | — |
| Serine | — | 0.1 | 0.1 | — | — |
| Arginine | — | — | 0.6 | — | — |
| Cystine | — | — | 0.1 | — | — |
| Histidine | — | — | 0.2 | — | — |
| Isoleucine | — | — | 0.4 | — | — |
| Leucine | — | — | 0.4 | — | — |
| Lysine | — | — | 0.4 | — | — |
| Methionine | — | — | 0.1 | — | — |
| Phenylalanine | — | — | 0.2 | — | — |
| Taurine | — | 0.1 | — | — | — |
| Threonine | — | — | 0.4 | — | — |
| Tryptophan | — | — | 0.05 | — | — |
| Tyrosine | — | — | 0.2 | — | — |
| Valine | — | — | 0.4 | — | — |
| HSA | — | 2 g/L | 2 g/L | yes | — |
| BSA | 5 mg/mL | — | — | — | 1 mg/mL | from Chapter 11 of Handbook of In Vitro Fertilization, 2nd ed., A. Trounson and D. Gardner, eds. (2000), incorporated herein by reference in its entirety.

TABLE 2

Irvine Scientific HTF media

| Component | mM |
|---|---|
| HTF | |
| Sodium Chloride | 97.8 |
| Potassium Chloride | 4.69 |
| Magnesium Sulfate, Anhydrous | 0.20 |
| Potassium Phosphate, Monobasic | 0.37 |
| Calcium Chloride, Anhydrous | 2.04 |
| Sodium Bicarbonate | 25.0 |
| Glucose | 2.7 |
| Sodium Pyruvate | 0.33 |
| Sodium Lactate | 21.4 |
| Gentamicin | 10 µg/mL |
| Phenol Red | 5 mg/L |
| Protein Supplementation | None (User Option) |
| Complete HTF with SSS | |
| Sodium Chloride | 91.44 |
| Potassium Chloride | 4.22 |
| Magnesium Sulfate, Anhydrous | 0.18 |
| Potassium Phosphate | 0.33 |
| Calcium Chloride | 1.84 |
| Sodium Bicarbonate | 22.50 |
| Glucose | 2.50 |
| Sodium Pyruvate | 0.30 |
| Sodium Lactate | 19.26 |
| Phenol Red | 4.5 mg/L |
| Gentamicin | 9 µg/mL |
| Human Serum Albumin | 5 mg/mL |
| Globulins | 1 mg/mL |
| Modified HTF | |
| Sodium Chloride | 97.8 |
| Potassium Chloride | 4.69 |
| Magnesium Sulfate, Anhydrous | 0.20 |
| Potassium Phosphate, Monobasic | 0.37 |
| Calcium Chloride, Anhydrous | 2.04 |
| Sodium Bicarbonate | 4.0 |
| HEPES | 21.0 |
| Glucose | 2.78 |
| Sodium Pyruvate | 0.33 |
| Sodium Lactate | 21.4 |
| Gentamicin | 10 µg/mL |
| Phenol Red | 5 mg/L |
| Protein Supplementation | None (User Option) |

TABLE 3

Irvine Scientific Single Step Medium ™

| Component | mM |
|---|---|
| Sodium Chloride | 101.5 |
| Potassium Chloride | 2.5 |
| Potassium Phosphate | 0.35 |
| Calcium Chloride, Anhydrous | 1.7 |
| Magnesium Sulfate, Anhydrous | 0.2 |
| Sodium Bicarbonate | 25.0 |
| Sodium Pyruvate | 0.2 |
| Glucose | 0.5 |
| Sodium Citrate | 1.0 |
| Sodium Lactate (D/L) | 20 |
| EDTA, Disodium, Dihydrate | 10 µM |
| Alanyl-glutamine | 1.0 |
| Alanine | 0.05 |
| Arginine | 0.3 |
| Asparagine | 0.05 |
| Aspartic Acid | 0.05 |
| Cysteine | 0.05 |
| Glutamic Acid | 0.05 |
| Glycine | 0.05 |
| Histidine | 0.1 |
| Isoleucine | 0.2 |
| Leucine | 0.2 |
| Lysine | 0.2 |
| Methionine | 0.05 |
| Phenylalanine | 0.1 |
| Proline | 0.05 |
| Serine | 0.05 |
| Taurine | 0.05 |
| Threonine | 0.2 |
| Tryptophan | 0.02 |
| Tyrosine | 0.1 |
| Valine | 0.2 |
| Phenol Red | 4.8 mg/L |
| Gentamicin | 10 µg/mL |

TABLE 4

Irvine Scientific P-1 ® (Preimplantation Stage One) Media ™

| Component | mM |
|---|---|
| P-1 ® Medium* | |
| Sodium Chloride | 101.6 |
| Potassium Chloride | 4.69 |
| Magnesium Sulfate, Anhydrous | 0.20 |
| Calcium Chloride, Anhydrous | 2.04 |
| Sodium Bicarbonate | 25 |
| Sodium Pyruvate | 0.33 |

TABLE 4-continued

Irvine Scientific P-1 ® (Preimplantation Stage One) Media ™

| Component | mM |
|---|---|
| Sodium Lactate | 21.4 |
| Taurine | 0.05 |
| Sodium Citrate | 0.15 mg/L |
| Phenol Red | 5 mg/L |
| Gentamicin | 10 µg/mL |
| Complete P-1 ® Medium with SSS ™ | |
| Sodium Chloride | 91.44 |
| Potassium Chloride | 4.22 |
| Magnesium Sulfate, Anhydrous | 0.18 |
| Calcium Chloride, Anhydrous | 1.84 |
| Sodium Bicarbonate | 22.50 |
| Sodium Pyruvate | 0.30 |
| Sodium Lactate | 19.26 |
| Taurine | 0.05 |
| Sodium Citrate | 0.14 mg/L |
| Phenol Red | 4.50 mg/L |
| Gentamicin | 9 µg/mL |
| Human Serum Albumin | 5 mg/mL |
| Globulins | 1 mg/mL |
| Complete P-1 ® Medium with DSS | |
| Sodium Chloride | 91.44 |
| Potassium Chloride | 4.22 |
| Magnesium Sulfate, Anhydrous | 0.18 |
| Calcium Chloride, Anhydrous | 1.84 |
| Sodium Bicarbonate | 22.50 |
| Sodium Pyruvate | 0.30 |
| Sodium Lactate | 19.26 |
| Taurine | 0.05 |
| Sodium Citrate | 0.14 mg/L |
| Phenol Red | 4.50 mg/L |
| Gentamicin | 9 µg/mL |
| Human Serum Albumin | 5 mg/mL |
| Dextran | 2 mg/mL |

TABLE 5

Irvine Scientific Early Cleavage Media ™

| Component | mM |
|---|---|
| Glucose | 0.50 |
| Sodium Chloride | 102.7 |
| Potassium Chloride | 2.50 |
| Magnesium Sulfate, Anhydrous | 0.20 |
| Calcium Chloride, Anhydrous | 1.70 |
| Sodium Bicarbonate | 25.0 |
| Sodium Pyruvate | 0.33 |
| Sodium Lactate (D/L) | 20.77 |
| Alanyl-glutamine | 0.50 |
| Taurine | 0.05 |
| Sodium Citrate | 0.15 mg/L |
| EDTA, disodium, dehydrate | 10 µM |
| Phenol Red | 4.8 mg/L |
| Gentamicin | 10 µg/mL |

TABLE 6

Irvine Scientific MultiBlast Media ™

| Component | mM |
|---|---|
| Sodium Chloride | 101.5 |
| Potassium Chloride | 2.5 |
| Potassium Phosphate | 0.35 |
| Calcium Chloride, Anhydrous | 1.7 |
| Magnesium Sulfate, Anhydrous | 0.2 |
| Sodium Bicarbonate | 25.0 |
| Sodium Pyruvate | 0.2 |
| Glucose | 3.0 |

TABLE 6-continued

Irvine Scientific MultiBlast Media ™

| Component | mM |
|---|---|
| Sodium Citrate | 1.0 |
| Sodium Lactate (D/L) | 20 |
| Alanyl-glutamine | 1.0 |
| Alanine | 0.05 |
| Arginine | 0.3 |
| Asparagine | 0.05 |
| Aspartic Acid | 0.05 |
| Cysteine | 0.05 |
| Glutamic Acid | 0.05 |
| Glycine | 0.05 |
| Histidine | 0.1 |
| Isoleucine | 0.2 |
| Leucine | 0.2 |
| Lysine | 0.2 |
| Methionine | 0.05 |
| Phenylalanine | 0.1 |
| Proline | 0.05 |
| Serine | 0.05 |
| Taurine | 0.05 |
| Threonine | 0.2 |
| Tryptophan | 0.02 |
| Tyrosine | 0.1 |
| Valine | 0.2 |
| Phenol Red | 4.8 mg/L |
| Gentamicin | 10 µg/mL |

In general, embryo culture media contains at least one energy substrate, at least one salt/ion, and preferably a buffer. Optionally, embryo culture media may contain at least one essential amino acid, at least one non-essential amino acid, at least one antioxidant, a pH indicator, and/or an antibiotic. In one embodiment, the components of the media set forth in Tables 1-6 can be modified up or down by up to about 40%, for example about 1%, about 2%, about 5%, about 10%, about 20%, or about 40%. In any case, the lactate concentration in the media is modified in accordance with the present invention.

In one aspect, the medium described herein comprises at least one energy substrate in addition to lactate. In one embodiment, the at least one additional energy substrate is pyruvate (e.g., sodium pyruvate). In one embodiment, the pyruvate is present between about 0 mM and about 3 mM, or any value or subrange there between. In a preferred embodiment, the pyruvate is present between about 0.1 mM and about 2.3 mM, or any value or subrange there between (e.g., about 0.1 mM, about 0.2 mM, about 0.3 mM, about 0.32 mM, about 0.33 mM, about 0.37 mM, about 0.5 mM, about 2.0 mM, about 2.27 mM). In one embodiment, pyruvate is present in the medium at one of the concentrations indicated in Tables 1-6 above.

In one embodiment, the at least one additional energy substrate is glucose. In one embodiment, glucose is present between about 0 mM and about 10 mM, or any value or subrange there between. In a preferred embodiment, glucose is present between about 0 mM and about 6.5 mM, or any value or subrange there between. In an especially preferred embodiment, glucose is present at less than about 3 mM, or any value or subrange there between (e.g., about 0.3 mM, about 0.5 mM, about 0.6 mM, about 0.8 mM, about 1.0 mM, about 1.5 mM, about 2.0 mM, about 2.5 mM, or about 3.0 mM). In one embodiment, no glucose is present. In one embodiment, glucose is present in the medium at one of the concentrations indicated in Tables 1-6 above.

In one aspect, the medium described herein comprises at least one salt. Salts that can be used in the medium described herein include, but are not limited to, sodium chloride, potassium chloride, magnesium sulfate, calcium chloride, potassium phosphate, sodium phosphate, cupric sulfate, ferric sulfate, and zinc sulfate.

In one embodiment, the medium comprises sodium chloride. In one embodiment, the sodium chloride is present in the medium at a concentration between about 65 mM and about 150 mM, or any value or subrange there between. In a preferred embodiment, sodium chloride is present in the medium at a concentration between about 85 mM and about 120 mM. In one embodiment, sodium chloride is present in the medium at a concentration between about 85 mM and about 110 mM. In one embodiment, sodium chloride is present in the medium at one of the concentrations indicated in Tables 1-6 above.

In one embodiment, the medium comprises potassium chloride. In one embodiment, potassium chloride is present at a concentration of between about 2 mM and about 10 mM, or any value or subrange there between. In a preferred embodiment, potassium chloride is present at a concentration of between about 2.5 mM and about 6 mM. In one embodiment, potassium chloride is present in the medium at one of the concentrations indicated in Tables 1-6 above.

In one embodiment, the medium comprises magnesium sulfate. In one embodiment, magnesium sulfate is present at a concentration of between about 0 mM and about 2 mM, or any value or subrange there between. In a preferred embodiment, magnesium sulfate is present at a concentration of between about 0.1 mM and about 1 mM. In one embodiment, magnesium sulfate is present in the medium at one of the concentrations indicated in Tables 1-6 above.

In one embodiment, the medium comprises calcium chloride. In one embodiment, calcium chloride is present at a concentration of between about 0 mM and about 5 mM, or any value or subrange there between. In a preferred embodiment, calcium chloride is present at a concentration of between about 1 mM and about 2.5 mM. In one embodiment, calcium chloride is present in the medium at one of the concentrations indicated in Tables 1-6 above.

In one embodiment, the medium comprises potassium phosphate. In one embodiment, potassium phosphate is present at a concentration of between about 0 mM and about 2 mM, or any value or subrange there between. In a preferred embodiment, potassium phosphate is present at a concentration of between about 0 mM and about 0.5 mM. In one embodiment, potassium phosphate is present in the medium at one of the concentrations indicated in Tables 1-6 above.

In one embodiment, the medium comprises sodium phosphate. In one embodiment, sodium phosphate is present at a concentration of between about 0 mM and about 2 mM, or any value or subrange there between. In a preferred embodiment, sodium phosphate is present at a concentration of between about 0 mM and about 0.8 mM. In one embodiment, sodium phosphate is present in the medium at one of the concentrations indicated in Tables 1-6 above.

In one embodiment, the medium comprises a buffer. Buffers and concentrations thereof for media solutions are well-known in the art. In one embodiment, the buffer is sodium bicarbonate. In one embodiment, sodium bicarbonate is present at a concentration of between about 0 mM and about 30 mM, or any value or subrange there between. In a preferred embodiment, sodium bicarbonate is present at a concentration of between about 20 mM and about 25 mM. In one embodiment, sodium phosphate is present in the medium at one of the concentrations indicated in Tables 1-6 above.

In one embodiment, the medium comprises at least one buffer. Buffers and concentrations thereof for media solutions are well-known in the art. In one embodiment, the buffer is HEPES. In one embodiment, HEPES is present at a concentration of between about 0 mM and about 30 mM, or any value or subrange there between. In one embodiment, the buffer is sodium bicarbonate. In one embodiment, sodium bicarbonate is present at a concentration of between about 0 mM and about 30 mM, or any value or subrange there between. In a preferred embodiment, the buffer is present at a concentration of between about 20 mM and about 25 mM. In one embodiment, the buffer is present in the medium at one of the concentrations indicated in Tables 1-6 above.

In one embodiment, the medium comprises at least one amino acid. In one embodiment, the medium comprises at least one essential amino acid. The essential amino acids include arginine, cysteine, histidine, isoleucine, leucine, lysine, methionine, phenylalanine, taurine, tryptophan, tyrosine, and valine. In one embodiment, the medium comprises at least one non-essential amino acid. The non-essential amino acids include alanine, asparagine, aspartate, glutamate, glycine, proline, and serine. In one embodiment, glutamine is present as alanyl-glutamine. In one embodiment, the at least one amino acid is present at a concentration of between about 0 mM and about 1.5 mM. In a preferred embodiment, the at least amino acid is present at a concentration of between about 0 mM and about 0.6 mM. In one embodiment, amino acid is present in the medium at one of the concentrations indicated in Tables 1-6 above.

In one embodiment, the medium comprises at least one antioxidant. Antioxidants and concentrations thereof for media solutions are well-known in the art. In one embodiment, the antioxidant is sodium citrate. In one embodiment, sodium citrate is present at a concentration of between about 0 mg/L and about 5 mg/L, or any value or subrange there between (e.g., about 0.1 mg/L, about 0.5 mg/L, about 1 mg/L, about 2 mg/L). In one embodiment, the antioxidant is EDTA. In one embodiment, EDTA is present at a concentration of between about 0 µM and about 50 µM, or any value or subrange there between (e.g., about 1 µM, about 5 µM, about 10 µM, about 25 µM, about 50 µM). In one embodiment, the antioxidant is present in the medium at one of the concentrations indicated in Tables 1-6 above.

In one embodiment, the medium comprises a pH indicator. In a preferred embodiment, the pH indicator is phenol red. In one embodiment, phenol red is present at a concentration of between about 0 mg/L and about 10 mg/L, or any value or subrange there between (e.g., between about 0 mg/L and about 5 mg/L, about 2 mg/L, about 3 mg/L, about 4 mg/L). In one embodiment, the pH indicator is present in the medium at one of the concentrations indicated in Tables 1-6 above.

In one embodiment, the medium comprises at least one antibiotic. Antibiotics and concentrations thereof for media solutions are well-known in the art. In one embodiment, the antibiotic is gentamicin sulfate. In one embodiment, the antibiotic is penicillin. In one embodiment, the antibiotic is streptomycin. In one embodiment, the antibiotic is present at a concentration between about 0 µg/mL and about 200 µg/mL, or any value or subrange there between (e.g., about 1 µg/mL, about 5 µg/mL, about 10 µg/mL, about 20 µg/mL, about 50 µg/mL, about 100 µg/mL). In one embodiment, the antibiotic is present at a concentration between about 0 IU/mL and about 500 IU/mL, or any value or subrange there between (e.g., about 1 IU/mL, about 5 IU/mL, about 10

IU/mL, about 20 IU/mL, about 50 IU/mL, about 100 IU/mL, about 250 IU/mL, about 500 IU/mL). IU=international units.

In one embodiment, the medium is supplemented with protein. In one embodiment, the protein is bovine serum albumin (BSA). In a preferred embodiment, the protein is human serum albumin (HSA). In one embodiment, the protein is alpha- and/or beta-globulins. In one embodiment, dextran is used as an alternative to globulins. In one embodiment, the medium comprises serum (e.g., human serum, horse serum, or bovine serum). In a preferred embodiment, the medium does not contain serum.

The embryo can be cultured in the medium for any desired period of time. For example, the embryo can be cultured for 24 hours up to 7 days or any time period or range there between after fertilization. Preferably, the embryo is cultured for 3-6 days before transfer. The embryo can be cultured until developmental milestones are met such as achieving a certain number of cells (e.g., 6-8 cells) or attaining a stage (e.g., the blastocyst stage). In some embodiments, a cryopreserved embryo is thawed and cultured using the methods described herein before transfer. In some embodiments, the embryo was cultured using methods as described herein prior to cryopreservation. In some embodiments, the embryo was not cultured using methods as described herein prior to cryopreservation.

The culturing can be performed utilizing any suitable incubation or culturing system or device with about 5% to about 6.5% $CO_2$ and maintaining at about 35° C. to about 40° C. In some aspects, a dedicated incubator is utilized. Non-limiting examples of incubators include the MINC™ incubator (Cook Medical), Labotect CO2 Mini Incubator (Origio MidAtlantic Devices), Origio Planer Benchtop Incubator BT37 (Origio), G185 IVF Tri-Gas Incubator (LabIVF), and the like. The methods further can include imaging systems that can obtain images of the embryos at one or more stages of development. In some embodiments, the incubator itself can include integrated imaging systems or devices. One example of such a device is the EmbryoScope incubator (Fertilitech).

The methods further can include, for example, culturing an embryo from at least one patient (female and/or male, e.g., mother and/or father) that is suffering from infertility, undergoing infertility treatment, and/or pursuing in vitro fertilization. The methods further can include culturing an embryo for a desired period of time, and then transferring the embryo into the mother, or cryopreserving the embryo.

Some embodiments relate to compositions and culture media including the modified media as described herein for embryo culture. Some embodiments relate to kits comprising one or more components for a media that has a lactate concentration as described herein. Some embodiments relate to incubators that comprise a media with or without an embryo, which media has a lactate concentration as described herein.

EXAMPLES

Additional embodiments are disclosed in further detail in the following examples, which are not in any way intended to limit the scope of the claims.

Example 1

Testing Protocol of Bovine Embryo Assay

On Day 0 (fertilization date), Wash dishes and Culture dishes were prepared with each corresponding testing medium. The dishes were equilibrated in a 39° C. incubator with 5% $CO_2$ overnight:

Wash dish: 100 uL Wash aliquots under oil for each testing medium
Culture dish: 50 uL Culture aliquots under oil for each testing medium On Day 1 after fertilization, fifty 1-cell embryos were washed in the Wash aliquots of each testing medium. About 10 eggs were evenly distributed into respective Culture aliquots. Two different media backbones were tested (Prototype A and CSCM-C).

The embryos were cultured for 8 days without disturbance in the incubator (39° C. with 5% $CO_2$).

Blastocyst development was observed and recorded on Day 6 and the results of the observations and recordings are illustrated in Table 7. A summary of Test 1 and Test 2 is provided in Table 7 and FIG. 1.

TABLE 7

Summary of bovine embryo assay for Prototype A and CSCM-C testing

| | Total embryos tested | Expanded + hatching blastocysts | % Expanded + hatching blastocysts |
|---|---|---|---|
| Test 1 | | | |
| Prototype A, 1 mM L-lactate | 38 | 9 | 23.7 |
| Prototype A, 5 mM L-lactate | 38 | 7 | 18.4 |
| CSCM-C, 1 mM L-lactate | 39 | 8 | 20.5 |
| CSCM-C, 6 mM L-lactate | 39 | 6 | 15.4 |
| Test 2 | | | |
| Prototype A, 1 mM L-lactate | 39 | 5 | 12.8 |
| Prototype A, 5 mM L-lactate | 39 | 2 | 5.1 |
| CSCM-C, 1 mM L-lactate | 38 | 9 | 23.7 |
| CSCM-C, 6 mM L-lactate | 38 | 7 | 18.4 |

| | Test 1 | Test 2 |
|---|---|---|
| Prototype A, 1 mM L-lactate | 23.7 | 12.8 |
| Prototype A, 5 mM L-lactate | 18.4 | 5.1 |
| CSCM-C, 1 mM L-lactate | 20.5 | 23.7 |
| CSCM-C, 6 mM L-lactate | 15.4 | 18.4 |

Example 2

Glucose Consumption by Bovine Embryos

Figure 2:
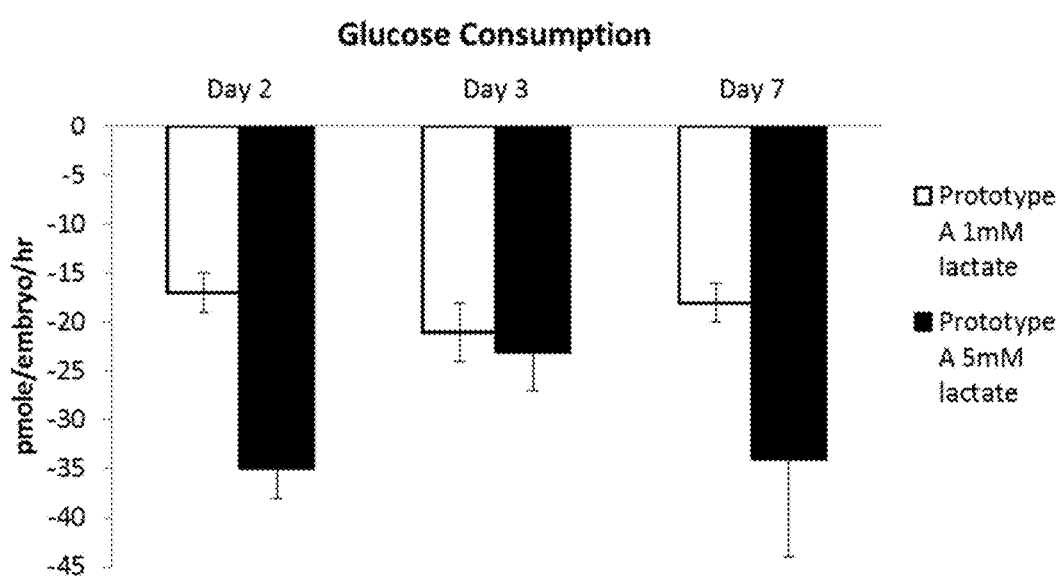
FIG. 2 represents glucose consumption by a bovine embryo after 2, 3, and 7 days of culture in 1 mM or 5 mM L-lactate-containing medium.

Bovine embryos were fertilized, washed, and cultured as described in Example 1 in Prototype A medium containing 1 mM or 5 mM lactate. Glucose consumption by the embryos was measured at day 2, day 3, and day 7 by culturing embryos from each time point individually in fresh drops of the respective culture medium (along with a respective control drop of medium not containing embryos) for a 24 hour period, and the spent and control media were then analyzed for glucose concentration to determine the amount consumed by embryos in each medium at each time point. Results are shown in FIG. 2. Briefly, these data demonstrate that less glucose is consumed by embryos in the low lactate medium (Prototype A, 1 mM), especially for the D2 (2-4 cell) and day 7 (blastocyst) stages.

Without being bound by theory, it is believed that viable preimplantation embryos have a "quieter" metabolism than do less viable embryos. That is, higher-quality embryos consume fewer nutrients (e.g., glucose oxygen, and other nutrients) than lower-quality embryos. Increased metabolism may be brought on by stress, which decreases embryo viability. See, e.g., Leese, et al., Mol. Human Reprod. 14(12), 667-672 (2008). Thus, the lower level of glucose consumption by embryos cultured with 1 mM lactate indicates healthier embryos. This supports the concept that low lactate medium is beneficial to viable embryo development in vitro.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

What is claimed is:

1. A method of culturing a human embryo in vitro, the method comprising culturing a human embryo in a medium comprising: a starting lactate concentration of between about 0.3 mM and about 1 mM, and a glucose concentration of less than about 2 mM, wherein the medium does not contain serum, wherein the medium is a sequential medium or a medium that is replenished at least once during the culturing of the embryo.

2. The method of claim 1, wherein the starting lactate concentration is about 1 mM.

3. The method of claim 1, further comprising culturing the embryo in an incubator.

4. The method of claim 3, wherein the incubator comprises an imaging system to capture one or more images of the embryo during culturing.

5. The method of claim 4, wherein the one or more images can be captured without moving the embryo.

6. The method of claim 1, wherein the medium is a modified version of any of the following: P-1 medium, G1 medium, G2 Medium, a Human Tubal Fluid (HTF) medium with or without glucose or phosphate, modified HTF medium, Whitten's Medium, Ham's F-10 Medium, or KSOM medium, with or without protein supplementation.

7. The method of claim 1, wherein said embryo is from a patient suffering from infertility or undergoing fertility treatment.

8. The method of claim 1, wherein said embryo is cultured for about 1 day to about 7 days.

9. The method of claim 8, wherein the embryo is cultured for about 3 days to about 6 days.

10. The method of claim 9, wherein the embryo is cultured until it reaches an 8-cell stage or a blastocyst stage.

11. The method of claim 1, further comprising implanting said embryo into a female patient.

12. A composition for culturing a human embryo, comprising an embryo culture medium suitable for culturing a human embryo and that is modified to have:
  (i) a lactate concentration of between about 0.3 mM and about 1 mM,
  (ii) a glucose concentration of less than about 2 mM,
  (iii) human serum albumin; and
  wherein the embryo culture medium does not contain serum.

13. The method of claim 1, wherein the medium further comprises human serum albumin.

14. The composition of claim 12, wherein the lactate concentration is about 1 mM.

15. The composition of claim 12, further comprising at least one additional energy substrate.

16. The composition of claim 15, wherein the energy substrate is pyruvate.

17. The composition of claim 16, wherein the pyruvate is present in the composition at a concentration of between about 0.1 mM to about 3 mM.

* * * * *